United States Patent
Robert (10) Patent No.: US 6,309,219 B1
(45) Date of Patent: Oct. 30, 2001

(54) PERIOTOME

(75) Inventor: Christopher Robert, Lambertville, NJ (US)

(73) Assignee: Karl Schumacher Dental Instrument Company, Inc., Southampton, PA (US)

( * ) Notice: Subject to any disclaimer, the term of this patent is extended or adjusted under 35 U.S.C. 154(b) by 0 days.

(21) Appl. No.: 09/505,819

(22) Filed: Feb. 17, 2000

(51) Int. Cl.$^7$ ........................................ A61C 3/02
(52) U.S. Cl. ................... 433/144; 433/165; 433/215
(58) Field of Search ........................... 433/144, 143, 433/141, 215, 165

(56) References Cited

U.S. PATENT DOCUMENTS

| | | | |
|---|---|---|---|
| 1,369,582 | * | 2/1921 | Wagner ............................. 433/144 |
| 1,503,610 | | 8/1924 | Smith . |
| 1,605,320 | | 11/1926 | Bates . |
| 1,605,322 | | 11/1926 | Bates . |
| 1,875,680 | * | 9/1932 | Van Horn ......................... 433/144 |
| 2,552,134 | | 5/1951 | Berliner . |
| 2,569,844 | | 10/1951 | Berliner . |
| 3,325,900 | | 6/1967 | Sohlberg . |
| 4,060,897 | | 12/1977 | Greenstein . |
| 4,259,069 | | 3/1981 | Lustig . |
| 4,270,902 | * | 6/1981 | Wiland ............................. 433/144 |
| 4,698,019 | | 10/1987 | Martin . |
| 4,854,867 | | 8/1989 | Meinershagen . |
| 5,024,600 | | 6/1991 | Kline . |
| 5,030,091 | | 7/1991 | Svanberg . |
| 5,127,833 | | 7/1992 | Kline . |
| 5,169,313 | | 12/1992 | Kline . |
| 5,169,314 | | 12/1992 | Long . |
| 5,913,682 | * | 6/1999 | Strate ............................... 433/143 |

FOREIGN PATENT DOCUMENTS

| | | | |
|---|---|---|---|
| 603190 | * | 4/1926 | (FR) ............................... 433/144 |
| 8304175 | * | 12/1983 | (WO) .............................. 433/144 |

OTHER PUBLICATIONS

Mueller, "Ginival Peritomy", Dental Cosmos, p. 1037, 1923.*

* cited by examiner

Primary Examiner—Todd E. Manahan
(74) Attorney, Agent, or Firm—Handal & Morofsky (57) ABSTRACT

A periodontal surgical instrument is disclosed which includes a handle with two ends. One end comprises a shank with a first cutting head preferably comprising a thin, flexible, angled blade for insertion to separate the gingival attachment and enter the P.D.L. space. The angulation and length are preferably suited to circumscribe the entire circumference of the root structure, all the way to the root apices. The other end comprises a spatula-shaped blade. The blade creates enough space for the introduction of extraction instruments in a controlled manner, and at locations dictated by the surgeon. A method of use is also described for this periodontal surgical instrument for procedures where extraction is desired.

47 Claims, 7 Drawing Sheets

PERIOTOME

TECHNICAL FIELD

This invention relates to dental exodontia for the extraction of teeth. More specifically, inventive instrument is designed to achieve the cutting of the fibrous attachment of the tooth to bone, formed of thousands of microscopic fibers, collectively referred to as the periodontal Ligaments, or PDL.

BACKGROUND

Teeth generally comprise an upper exposed portion, or crown, which is visible and an underlying root structure which is hidden, being anchored within the bony substructure of the gums. The interface between the root structure of the tooth and the surrounding bone is a fibrous attachment. These fibers are referred to as the periodontal ligaments or PDL. The space occupied by the periodontal ligaments is known as the PDL space, and averages about 0.25 mm in thickness and surrounds the entire root structure of the tooth.

It is necessary to separate the ligamental attachment during various surgical procedures. Such procedures include the extraction of teeth, and the installation of dental implants and common surgery to remove roots broken during extraction or through trauma. While extraction is one of the most common dental procedures it is fraught with difficulty. The great forces employed to dislodge teeth from bone are difficult to control and so, have unpredictable outcomes.

One of the main obstacles in the removal of teeth is to overcome the resistance of the PDL. The most common method used to overcome this resistance is bucco-lingual luxation, which expands the socket by loosening of the tooth by grasping with a forceps and rocking the tooth in all directions in order to compress the proximate, relatively spongy portion of the surrounding bone, and stretch the periodontal ligaments until they break. Great force is needed to accomplish this, and the frequent result is fracture of the tooth or fracture of the surrounding bone that forms the buccal plate. Both of these problems lead to further surgical complications.

In the case of a fractured crown, it is often necessary to resort to a full-surgical extraction, elevating the soft tissue and removing bone, in order to gain access to the retained root. Full surgical procedures are time-consuming, traumatic to the patient, and carry more risk of infection and healing complications. In the case of a fractured buccal plate, the bone loses its blood supply, and will resorb away. Soft tissues will epithelialize faster than the bone will regenerate, and the remaining portion of the gum which formerly supported the tooth, also known as the ridge, will display a depression or defect. Loss of the bony architecture and its replacement by soft tissues, further complicates the prosthetic treatment plan. Indeed, in such a scenario, it is likely that a bone graft will be required. In other words, conventional crown and bridge prosthesis require bony support, and replacement of the tooth with an implant requires healthy surrounding bone. Often, it is necessary to do a separate preliminary surgery (Guided Bone Regeneration) to repair a defect before an implant is placed.

While instruments capable of the cutting the PDL are known to be used in connection with the extraction of teeth, such instruments fail to have the range and configuration necessary to effectively perform this function. In addition, such prior art instruments are clumsy to work with and have limited functionality in connection with such cutting, because they are often too thick, or improperly angled.

SUMMARY OF THE INVENTION

It is an object of the invention to remedy the deficiencies of the prior art heretofore discussed.

It is a further object of the invention to provide an instrument which allows the separation of the ligamental attachment without destroying the buccal plate.

It is a further object of the invention to provide an instrument with two functional tools which function synergistically to allow the user to separate the ligamental attachment and allow teeth to escape the bone occlusally.

It is a further object of the invention to provide a method which allows the separation of the ligamental attachment while minimizing damage to the buccal plate.

The invention is directed to a dental instrument, namely a periotome. The inventive instrument is of particular value because it also comprises a handle having two tools. At one end there is a tool with a thin, flexible, angled blade for insertion to separate the gingival attachment and enter the PDL space. The angulation and length are suited to circumscribe the entire circumference of the root structure, all the way to the root apices. At the other end of the inventive periotome there is a second tool which comprises a larger, spatula-shaped member tapering into a triangular tipped blade having a size and thickness adapted to create space for the introduction of extraction instruments in a controlled manner, after the cutting out the PDL, and at locations dictated by the surgeon. The preservation of bone eliminates the need for follow-up repair of the ridge, simplifying the prosthetic treatment plan. In other words, the invention addresses the inefficiency of destroying the fibrous attachment by tearing apart the periodontal ligaments. Rather, in accordance with the invention, the ligaments are incised, with substantially no trauma to the surrounding bone. The handle is preferably made of hollow stainless steel, aluminum alloy or other lightweight material which makes it comfortable and easy to control.

BRIEF DESCRIPTION OF THE DRAWINGS

Some embodiments of the invention will now be described in detail, by way of example, with reference to the accompanying drawings which illustrate the invention.

DETAILED DESCRIPTION OF THE PREFERRED EMBODIMENTS

Figure 1:
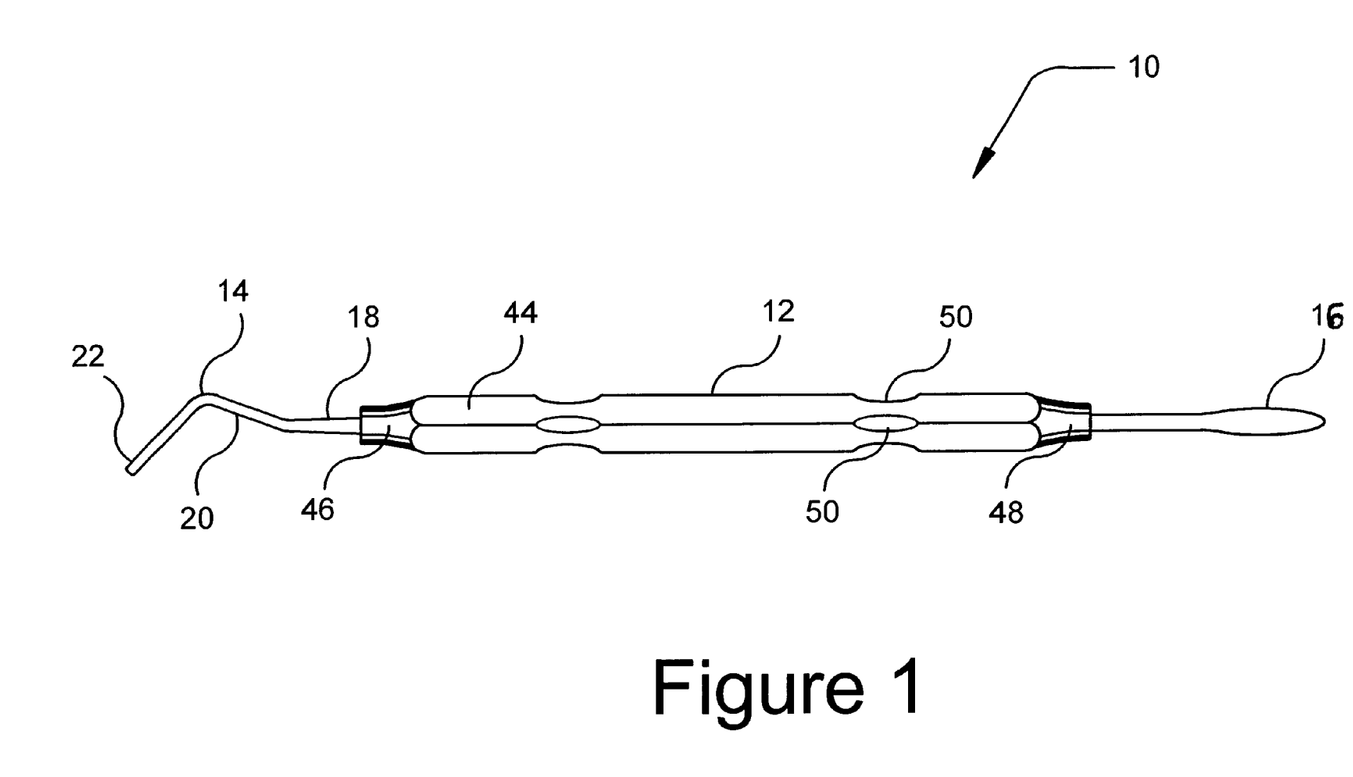
FIG. 1 is a side elevational view of a preferred embodiment of the invention.

FIG. 1 shows a preferred embodiment of the inventive periotome 10. Periotome 10 comprises a handle 12 with two functional tools 14 and 16 secured at each of its ends. In preferred embodiments, the cutting surfaces of the tools are coated with titanium nitride so that the blades remain sharp.

Figure 2:
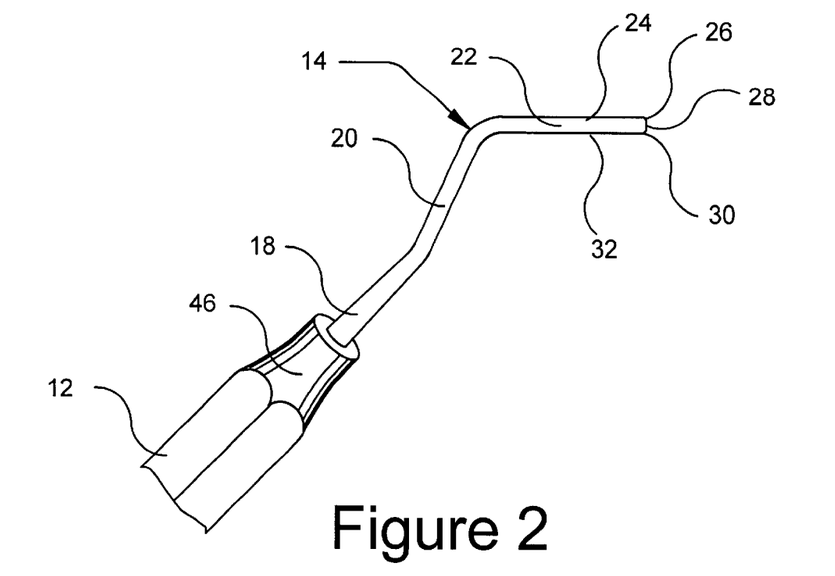
FIG. 2 is a detailed side view of a portion of the instrument shown in FIG. 1 showing the first tool.

As seen most clearly from FIG. 2, tool 14 preferably comprises three sections, a base 18, a stem 20, and a blade 22. Base 18, stem 20 and blade 22 are all formed from a single piece of metal. Base 18, stem 20 and blade 22 are connected at angles with rounded corners for safety. The angulation and length of the sections of tool 14 are suited to circumscribe the entire circumference of the root structure, all the way to the root apices.

Figure 3:
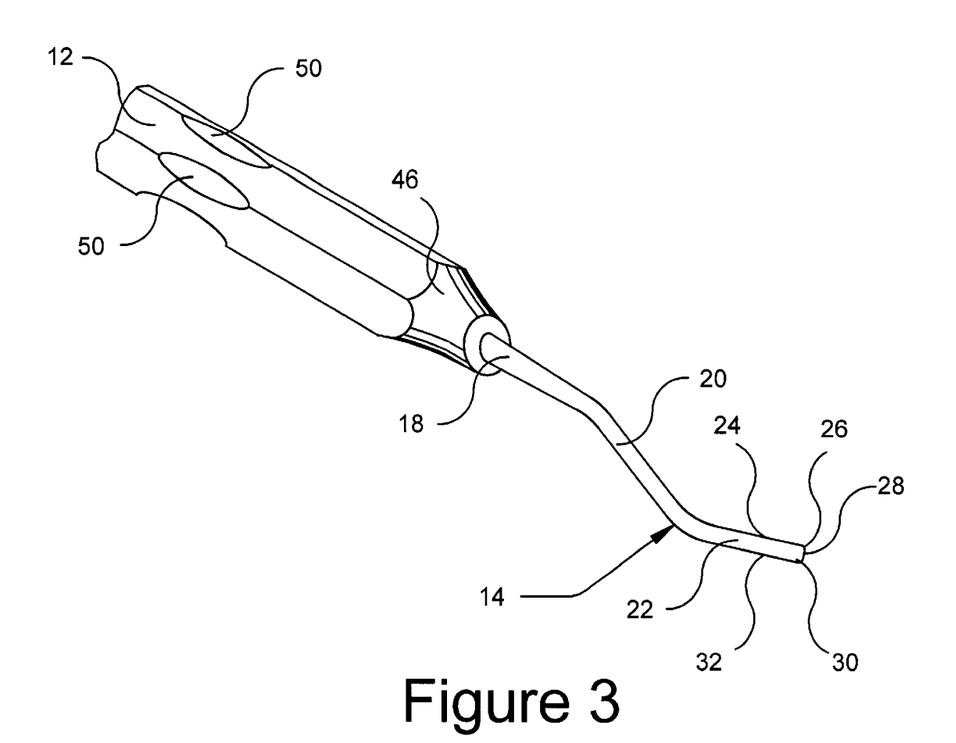
FIG. 3 is a detailed perspective view of a portion of the instrument shown in FIG. 1 showing the first tool.

Base 18 is formed as a roughly frustro conical member which tapers into stem 20. The length of base 18 is between 5–15 mm, preferably 10 mm. Its larger diameter adjacent handle 12 is 2.54 mm. Stem 20 is set at an angle of between 120–170 degrees, preferably 140° in one direction from base 18. Stem 20 is formed as a continuing frustro conical member which tapers into blade 22. The length of stem 20 is between 5–15 mm, preferably 8.89 mm while the larger diameter is between 1–2 mm, preferably 1.524 mm. Blade 22 is set at an angle of between 20 and 45 preferably 39° degrees in the opposite direction with respect to stem 20. The sharp angle allows the user to get into a smaller area without hitting other teeth. Blade 22 is formed with a substantially rectangular shape and is flat with a thickness of 0.4572 mm, and a width of 1.778 mm. Blade 22 preferably comprises a continuous cutting edge defined by five cutting surfaces 24, 26, 28, 30, and 32 as shown in FIGS. 2 and 3. Surfaces 24 and 32 are used to cut in the mesio-distal direction. Surface 28 is used to cut in the apical direction. Surfaces 26 and 30 are rounded points which can be used to cut in the apical direction.

Figure 4:
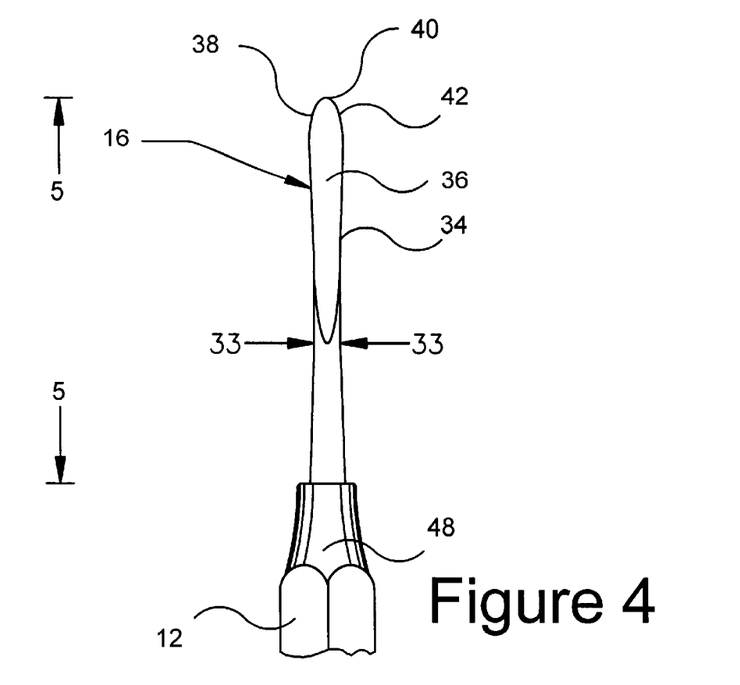
FIG. 4 is a detailed side elevational view of a portion of the instrument shown in FIG. 1 showing the second tool.

As shown in FIG. 4, tool 16 is formed from a member 34 which first tapers inwardly then outwardly into a spatula-shaped blade 36. In accordance with the preferred embodiment illustrated in FIG. 1, tool 16 has a length of about 25.4 mm. Member 34 has a thickness at point 31 of between 2 and 6 mm, preferably 3.30 mm in the direction of the plane of the drawing. It then tapers inwardly to a thickness of between 0.5 and 2.5 mm, preferably 1.9 mm at point 33 in the direction of the plane of the drawing of FIG. 4. Member 34 then flattens and expands to a width of between 2 and 6 mm, preferably 2.54 mm in the direction of the plane of the drawing. Member 34 preferably has a circular cross section point 31 and point 33.

Figure 5:
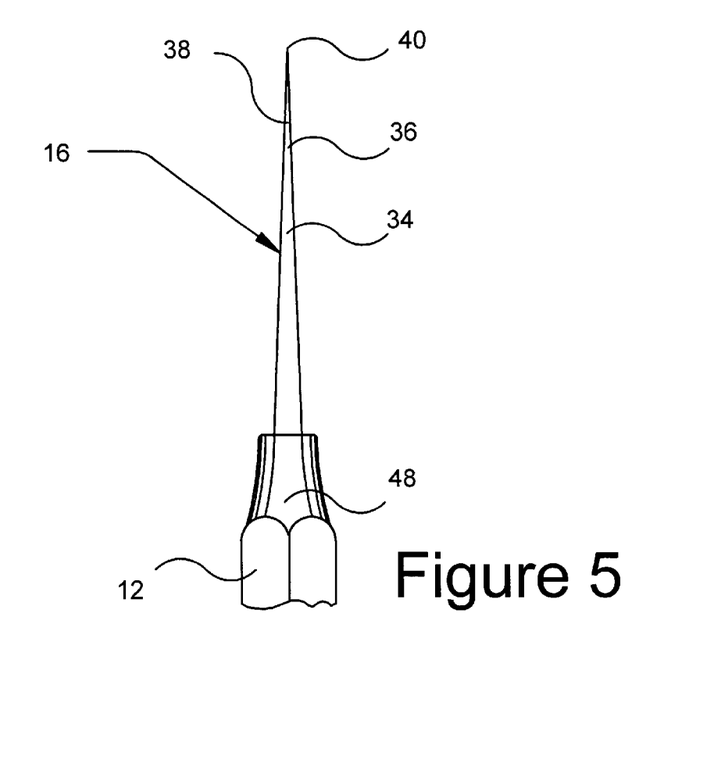
FIG. 5 is a detailed view along lines 5—5 of FIG. 4 showing other aspects of the configuration of the second tool.

FIG. 5 shows a side view of triangular tipped blade 36. Blade 36 is of a size and thickness so that the surgeon creates enough space for the introduction of extraction instruments in a controlled manner, and at locations dictated by the surgeon. More particularly, at point 35, the blade has a thickness on the order of between 1 and 3 mm, preferably 1.27 mm in the direction of the plane of the drawing of FIG. 5. From there it terminates in a point. Blade 36 is preferably triangular in shape with three cutting surfaces, 38, 40, and 42. The length of blade 36 is about 37.4 mm. The angle of the tip is about 40 degrees.

Figure 6:
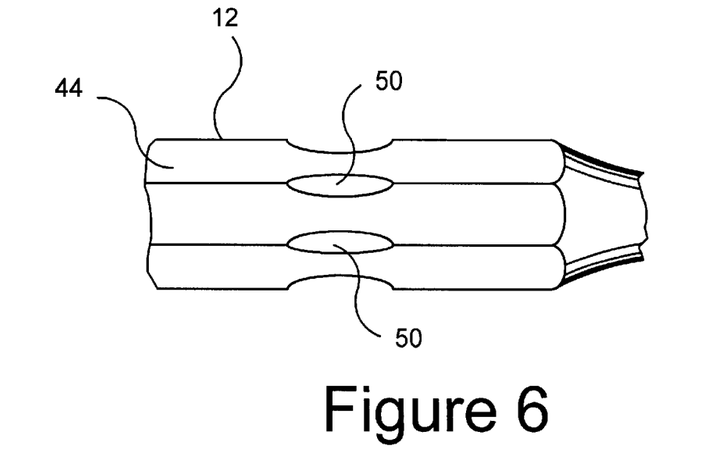
FIG. 6 is a detailed side view of the embodiment shown in FIG. 1 showing part of the handle.

Handle 12 is preferably made of hollow stainless steel. It is preferably lightweight, weighing about between 0.2 oz. and 2.0 oz., preferably 0.8 oz. These parameters make handle 12 comfortable and easy to control. Handle 12 preferably comprises a center section 44 and two roughly frustro conical end sections 46 and 48. Center section 44 comprises a hollow tube which is formed for comfort to the user. In preferred embodiments, the tube has a triangular or hexagonal cross section so that the tool rests comfortably between the fingers. The length of center section 44 is between 60 and 120 mm, preferably 90 mm. Center section 44 has a diameter which is between 5 and 30 mm, preferably 11 mm. In preferred embodiments, center section 44 also comprises a plurality of support indentations or ridges 50 placed at points approximately ¼ and ¾ of the length of center section 44. The dimensions of the handle are balanced to reduce hand fatigue (where a larger diameter is preferred) with functionality as a dental instrument (where a smaller diameter is preferred). The larger diameter is available due to the angulation of tool 14 as the provision of at least three cutting surfaces on the tool to allow greater flexibility in smaller spaces as well the use of frustro conical tapered end sections 46 and 48.

Figures 7, 8, 10:
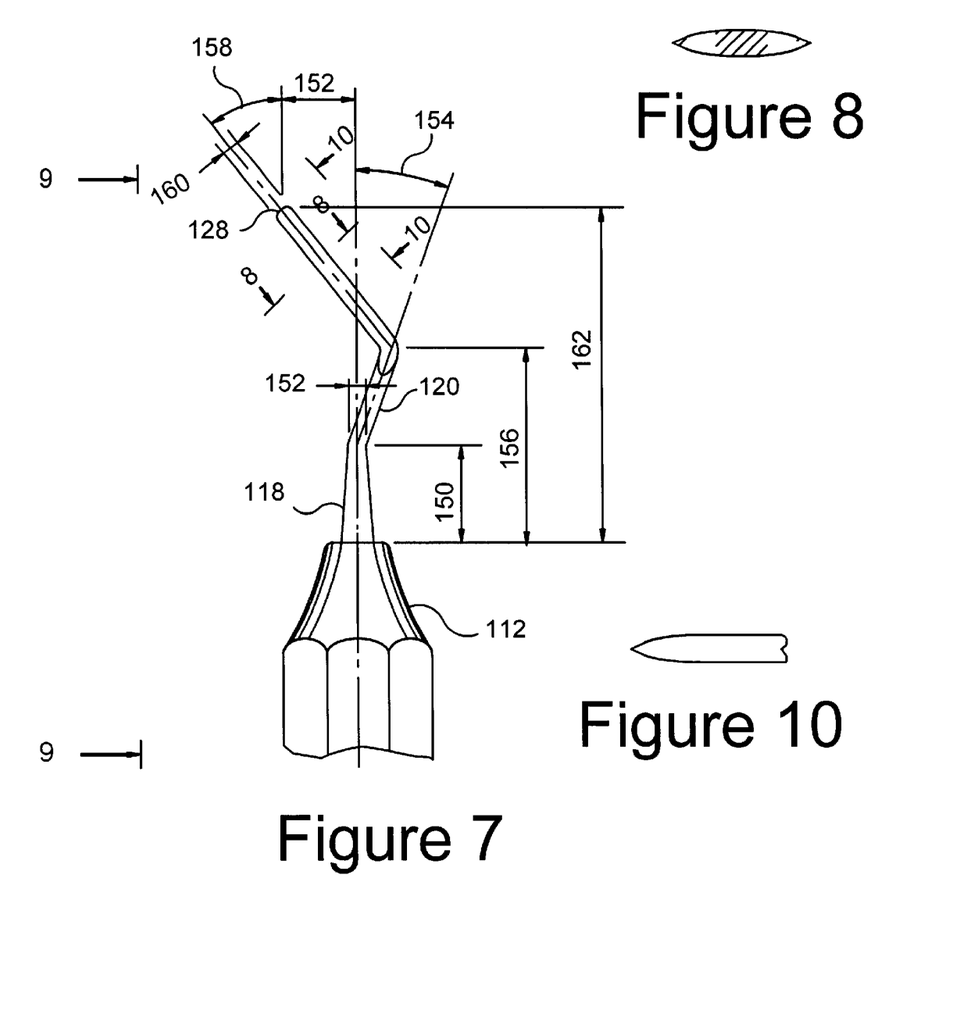
FIG. 7 is a front view of a portion of the instrument shown in FIG. 1 showing a second embodiment of the first tool.
FIG. 8 is a side view of FIG. 7 across lines 8—8.
FIG. 10 is a side view of FIG. 7 across lines 10—10.
Figure 9:
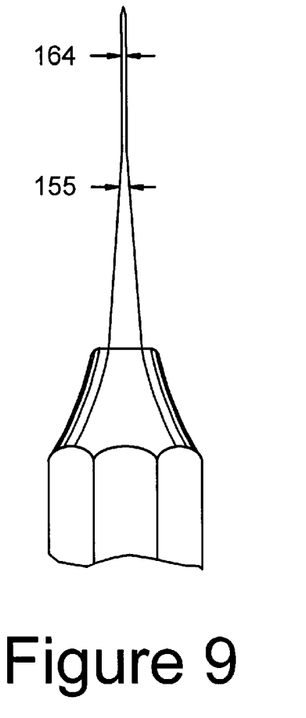
FIG. 9 is a side view of FIG. 7 across lines 9—9.

FIG. 7 shows a second preferred embodiment of the inventive periotome 110 which is similar in configuration to periotome 10. Base 118 is formed as a roughly frustro conical member which tapers into stem 120. The length 150 of base 118 is between 7 and 10 mm, preferably 8.6 mm. Diameter 152 is about 1.9 mm. Stem 120 is set at an angle 154 of 20 degrees, from base 118. Stem 120 is formed as a continuing frustro conical member which tapers into blade 122. The length of stem 120 is preferably 16 mm while the larger diameter 155 is about 1.4 mm as shown in FIG. 9 which is a side view taken across lines 9—9 of FIG. 7. The vertical distance 156 from the top of stem 120 to the bottom of base 118 is about 17.35 mm. Blade 122 is set at an angle 158 of about 39 degrees from base 118 in the opposite direction. A side view of blade 122 across lines 8—8 is shown in FIG. 8. The length 160 of blade 128 is about 1.88 mm. The vertical distance 162 of blade 122 to base 112 is about 30 mm. The thickness 164 of blade 122 is about 5.3 mm. The shape between cutting surfaces 126 and 128 is a radius of about 0.031 inches. FIG. 10 is a side view across lines 10—10.

Figure 11:
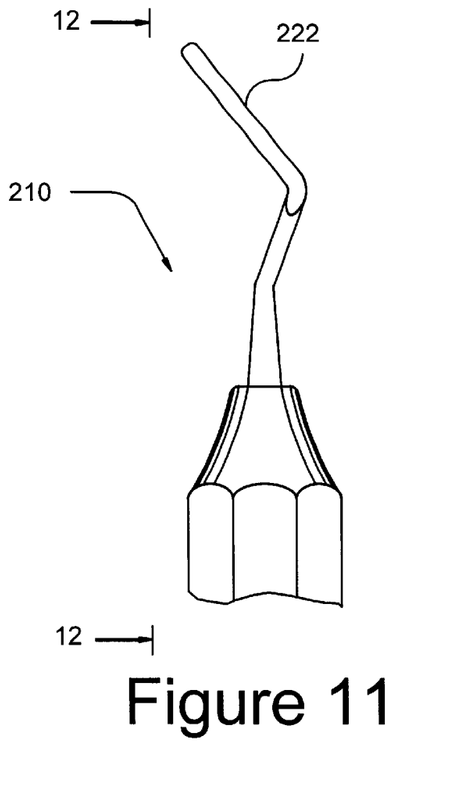
FIG. 11 is a front view of a portion of an alternative embodiment of the inventive periotome.
Figure 12:
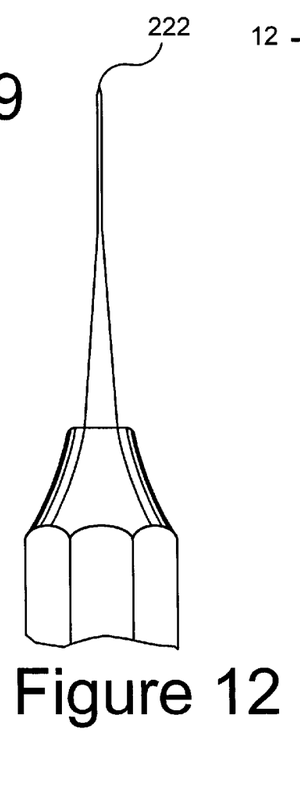
FIG. 12 is a side view of FIG. 7 across lines 12—12.

FIG. 11 shows another embodiment of the inventive periotome. Periotome 210 is similar in configuration to periotomes 10 and 110. However, blade 222 is now rotated between 20 to 80 degrees, ideally between 37 and 52 degrees, preferably about 45 degrees. The rotated blade allows the surgeon to come in from the front of the mouth and reach, for example, the interior portion of the back molars. FIG. 12 is a side view across lines 12—12. Without the angulation it is difficult for the surgeon to cut straight down into the gum line to separate the tooth because the cheek is in the way. A second cutting tool may be secured to the other end of handle 212. This second cutting tool has a configuration which is a mirror image of cutting tool 214.

Figures 16, 17:
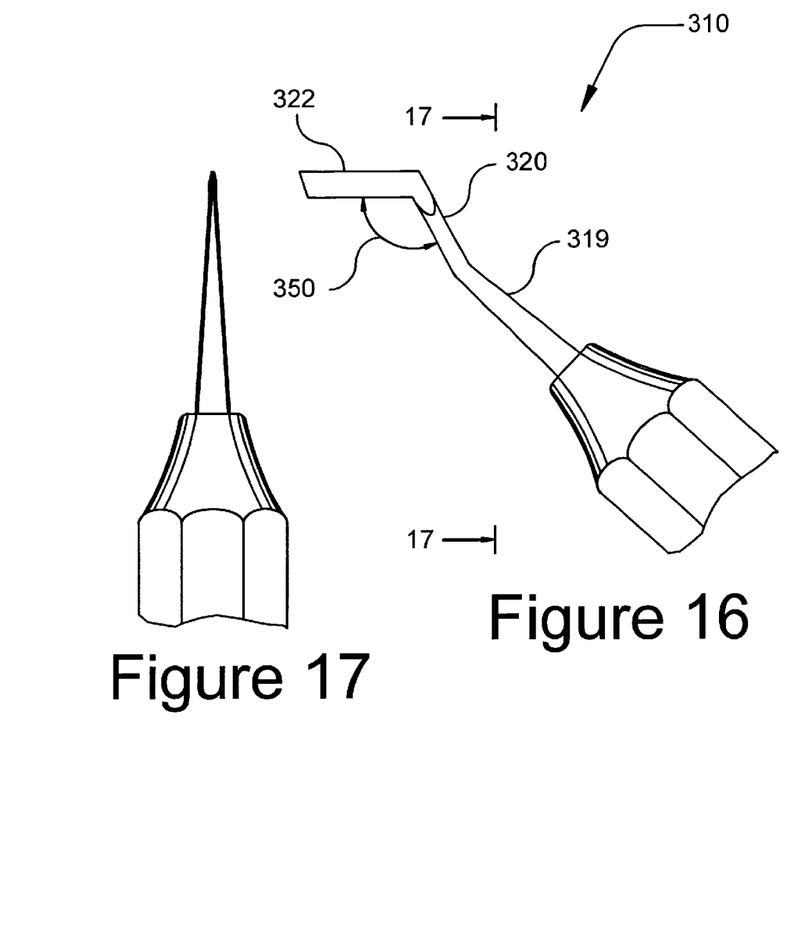
FIG. 16 is a front view of a portion of the instrument shown in FIG. 1 showing a fourth embodiment of the first tool.
FIG. 17 is a side view of FIG. 16 across lines 17—17.

FIG. 16 shows a fourth preferred embodiment of the inventive periotome 310 which is similar in configuration to periotome 110. However the angulation 350 of blade 322 from stems 319 and 320 is deeper. FIG. 17 is a side view taken along lines 17—17.

Figures 18, 19:
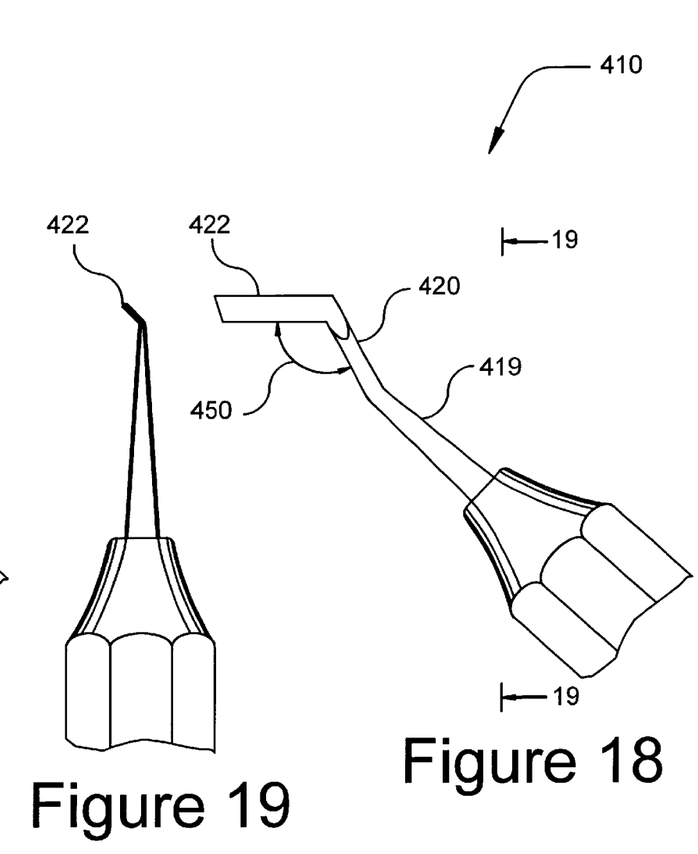
FIG. 18 is a front view of a portion of the instrument shown in FIG. 11 showing a fifth embodiment of the first tool.
FIG. 19 is a side view of FIG. 16 across lines 19—19.

FIG. 18 shows a fifth embodiment of the inventive periotome 410 which is similar in configuration to periotome 310 with blade 422 rotated between 20 to 80 degrees, ideally between 37 and 52 degrees, preferably about 45 degrees. FIG. 17 is a side view taken along lines 17—17.

In practice, the surgeon will use tool 14 to come in from the occlusal direction and cut into the PDL space about 12 mm or so. The five cutting surfaces 24, 26, 28, 30, and 32 and flexibility of blade 22 allows the surgeon to come in from the side without hitting the jaw. Then the surgeon will gently insert triangular tipped blade 36 of tool 16 into the space made with tool 14. Then the surgeon will rock blade 36 back and forth so that cutting surfaces 38, 40, and 42 will gently expand the ridge of the socket with minimal compression to the bone without damaging the bone until there is enough space for the introduction of extraction instruments in a controlled manner, and at locations dictated by the surgeon. Normally, anatomy, i.e., proximity of other teeth, etc. dictates where elevators and forceps are applied. Here site of application is formed by blade 36 where surgeon can take advantage of greater bone mass. It is noted that the working tips of the instrument of the present invention are made of stainless steel. After being forged, the same are heat treated and sharpened. After being heat treated, tool 16 is formed into a specialized wedge to work as an adjunct to the cutting tip 14.

Figure 13:
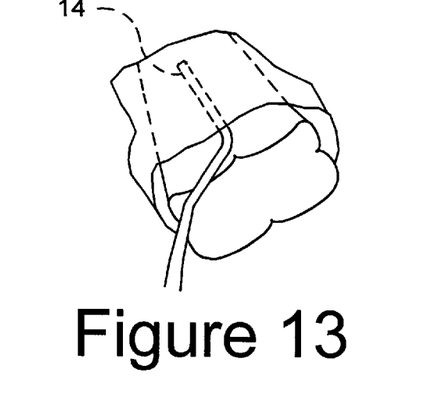
FIG. 13 is a perspective view of the scalpel or incisor tip being inserted into the PDL space on the buccal aspect of a maxillary right first molar.
Figure 14:
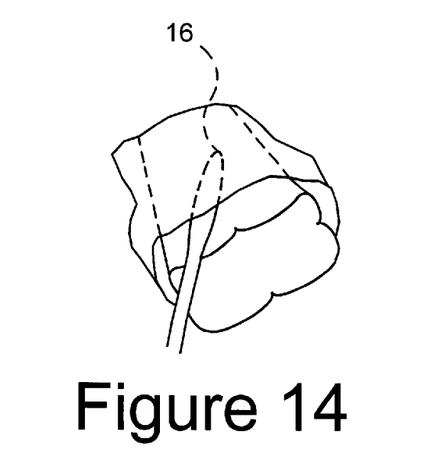
FIG. 14 is a perspective view of the separator blade of the present invention being inserted into the PDL space on the mesial aspect of the same tooth.
Figure 15:
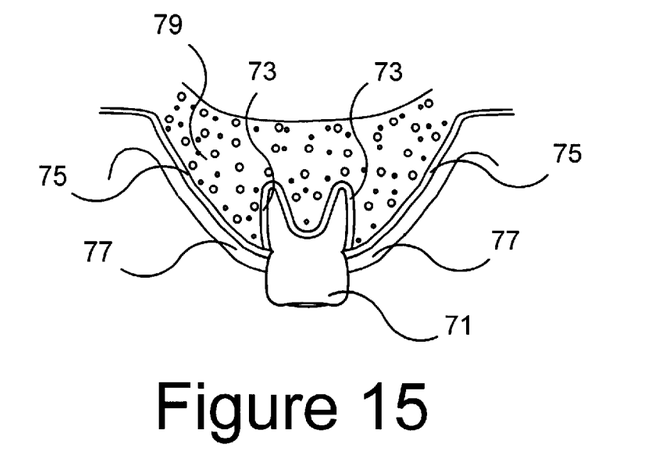
FIG. 15 shows typical anatomy of a maxillary right first molar, surrounding bone and soft tissues, as viewed from the mesial aspect.

As can be seen in FIG. 13, the proper orientation of cutting tip 14 is substantially parallel to the axis of the tooth, allowing it to be advanced in the direction of the axis of the tooth into the periodontal ligament space on the buccal aspect of a maxillary right first molar. After tip 14 has been inserted into the space, it is carefully worked along the surface of the tooth to create a space to allow tip 16 to be inserted as shown in FIG. 14. This is better understood with reference to FIG. 15 which shows typical anatomy of a maxillary right first molar, and surrounding bone and soft tissues, as viewed from the mesial aspect in cross-section. This anatomy includes the maxillary right first molar 71, the periodontal ligaments 73 completely surrounding the root structure and attaching it to bone, the cortical bone plate 75, and the gingival soft tissues 77. During use of the subject instrument, the objective is to cut as much of the periodontal ligaments 73 as possible, for removal without destruction of the soft bone 79.

While some illustrative embodiments of the invention have been described above, it is, of course, understood that various modifications will be apparent to those of ordinary skill in the art. Such modifications are within the spirit and scope of the invention, which is limited and defined only by the appended claims.

What is claimed is:

1. A dental instrument comprising
   a) a handle having two ends;
   b) a first tool comprising a cutting blade configured and dimensioned for severing fibrous bony attachments, said blade being mounted at one of said ends; and
   c) a second tool mounted at the other end of said handle, said second tool comprising a blade comprising a blade tip portion, said blade tip portion being tapered in a first plane, said tapering in said first plane varying from a very narrow width adjacent said tip to widths progressively larger in the direction towards said other end of said handle, said blade tip portion further comprising a blade base portion having a width in said first plane equal to or less than the widest portion of said tip portion, and having a thickness in a plane transverse to said first plane substantially less than the width of the widest portion of said tip portion, said blade having a size and thickness adapted to create additional space for the introduction of extraction instruments in a controlled manner.

2. A dental instrument according to claim 1 wherein said cutting blade is flexible.

3. A dental instrument according to claim 1 wherein said first tool has a length and a width and is oriented with said length at an angle with respect to said handle, said angle having a magnitude and said length having a magnitude which render said first tool suited to circumscribe the entire circumference of the root structure to the root apices.

4. A dental instrument according to claim 1 wherein said first tool comprises:
   a) a base having a first end and a second end, said first end being connected to said handle;
   b) a stem having a length, a first stem end and a second stem end, said first stem end being connected to said second end of said base; and
   c) a blade portion having a first blade end and a second blade end, said first blade end being connected to said second stem end.

5. A dental instrument according to claim 4 wherein said base has a length and comprises a roughly frustro conical member, said roughly frustro conical member tapering into said stem.

6. A dental instrument according to claim 5 wherein said length of said base is between 5 and 15 mm.

7. A dental instrument according to claim 5 wherein said length of said base is 10 mm.

8. A dental instrument according to claim 4 wherein said cutting blade defines a substantially rectangular shape and is substantially flat with a thickness about 0.53 mm.

9. A dental instrument according to claim 4 wherein said stem comprises a substantially frustro conical member which tapers into said blade.

10. A dental instrument according to claim 4 wherein said length of said stem is between 5 and 15 mm.

11. A dental instrument according to claim 4 wherein said length of said stem is about 9 mm.

12. A dental instrument according to claim 4 wherein said blade is oriented at an angle of between 25 and 55 degrees with respect to said stem.

13. A dental instrument according to claim 12 wherein said stem is oriented at an angle of between 120 and 170 degrees with respect to said base.

14. A dental instrument according to claim 13 wherein said blade defines at least five cutting surfaces.

15. A dental instrument according to claim 1 wherein said blade defines at least three cutting surfaces.

16. A dental instrument according to claim 1 wherein said second tool comprises a triangular tipped blade.

17. A dental instrument according to claim 16 wherein said triangular tipped blade comprises three cutting surfaces.

18. A dental instrument according to claim 16 wherein said triangular tipped blade has a length, said length being about 25 mm.

19. A dental instrument according to claim 1 wherein said second tool has a length, said length being about 37.4 mm.

20. A dental instrument according to claim 1 wherein said handle comprises a center section and two frustro conical end sections.

21. A dental instrument according to claim 20 wherein said center section of said handle has a diameter of about 11 mm.

22. A dental instrument according to claim 21 wherein said center section of said handle has a hexagonal cross section.

23. A dental instrument according to claim 20 wherein said center section of said handle has a triangular cross section.

24. A dental instrument according to claim 1 wherein said handle weighs approximately 0.8 oz.

25. A dental instrument according to claim 1 wherein said handle comprises a center section and two end sections, said center section comprises a plurality of support indentations having a size and depth adapted to support a user's fingers while holding said dental instrument.

26. A dental instrument according to claim 1, wherein said first tool is connected to said handle by way of an intermediate support member having a first end and an opposing end, said first end of said intermediate support member being attached to said one end of said handle at a first angle with respect to said handle, said opposing end being attached to said blade at a second angle with respect to said blade, said second angle extending in a direction opposite said first angle.

27. A dental instrument according to claim 1, wherein said cutting blade is thin and substantially flat.

28. A dental instrument according to claim 1, cutting blade has at least three cutting surfaces.

29. A dental instrument according to claim 1, wherein said blade tip, after tapering from a small width to a large width in said blade tip portion, continues to taper to a small width in the direction towards said handle.

30. A dental instrument according to claim 1, wherein said cutting blade, being substantially flat and defining a plane which is oriented obliquely at a first angular orientation with respect to the plane defined by the intersection of said handle and said first tool.

31. A dental instrument as in claim 30, wherein the angular orientation of the blade portion is approximately 45 degrees relative to the base.

32. A dental instrument comprising:
 (a) a handle having two ends and adapted to be grasped by the user;
 (b) a first cutting tool secured to one end of said handle, said cutting tool comprising:
  i. a base portion secured to said one end of said handle and extending substantially in the same direction as said handle,
  ii. a second portion extending from said base portion, said second portion being secured integrally with said base portion, said second portion extending at an angle in a first direction with respect to said base portion, and
  iii. a blade portion extending from and integrally secured to said second portion, said blade portion extending at an angle with respect to said base portion in the direction opposite said first direction, the angle between said base portion and said second portion being large relative to the angle which said second portion and said blade portion make, said blade having a flattened configuration angularly aligned to be parallel to an inside surface and made to where said instrument is placed in a convenient position with respect to a tooth during use of the dental instrument on said tooth.

33. the dental instrument as in claim 32 further comprising a second cutting tool secured to the other end of said handle, said second cutting tool having a configuration which is a mirror image of said first cutting tool.

34. The dental instrument as in claim 32 wherein said blade portion is rotated 20 to 60 degrees relative to the base portion.

35. A dental instrument according to claim 34, wherein said first angle is greater then said second angle.

36. The dental instrument as in claim 32 wherein said blade portion is rotated about 45 degrees relative to the base portion.

37. The dental instrument as in claim 36 further comprising a second cutting tool secured to the other end of said handle, said second cutting tool having a configuration which is a mirror image of said first cutting tool.

38. A dental instrument comprising
 a) a handle having with two ends;
 b) a first tool comprising an cutting blade configured and dimension for severing fibrous bony attachments, said blade being mounted at one of said ends, said cutting blade being substantially and defining a plane which is oriented obliquely at a first angular orientation with respect to the plane defined by the intersection of said handle and said first tool; and
 c) a second tool which is a mirror image of said first tool, said second tool being mounted at the opposite end of said handle, said cutting blade being substantially flat and defining a plane which is oriented obliquely with respect to the plane defined by the intersection of said handle and said first tool with an angular orientation opposite said first angular orientation.

39. A dental instrument as in claim 38, wherein the angular orientation of the blade portion is approximately 45 degrees relative to the base.

40. A dental instrument as in claim 38, wherein said blade portion has a length and a width, said length being approximately eight times said width.

41. A dental instrument as in claim 40, wherein said blade portion has an angular orientation between −45 and 45 degrees.

42. A dental instrument as in claim 40, wherein said blade portion has an angular orientation of 0 degrees.

43. A dental instrument as in claim 40, wherein said blade portion has two opposing cutting surfaces.

44. A surgical kit comprising
 a) the dental instrument of claim 1; and
 b) the dental instrument of claim 38.

45. A surgical kit comprising
 a) the dental instrument of claim 1; and
 b) the dental instrument of claim 41.

46. A surgical kit comprising
 a) the dental instrument of claim 38; and
 b) the dental instrument of claim 41.

47. A method of extracting a tooth comprising the steps of:
 a) using a first tool to cut into the periodontal ligaments to provide a space; and
 b) inserting a second tool into said space and rocking said second tool back and forth to expand a boney socket surrounding said tooth.

* * * * *